(12) United States Patent
Kobal et al.

(10) Patent No.: US 12,185,750 B2
(45) Date of Patent: Jan. 7, 2025

(54) ACYL NORNICOTINES REDUCE SENSORY IRRITATION IN TOBACCO AND NICOTINE PRODUCTS

(71) Applicant: Altria Client Services LLC, Richmond, VA (US)

(72) Inventors: Gerd Kobal, Sandy Hook, VA (US); Douglas R. Oliveri, Powhatan, VA (US); Peter Reeh, Erlangen (DE); Tatjana Kichko, Erlangen (DE)

(73) Assignee: Altria Client Services LLC, Richmond, VA (US)

(*) Notice: Subject to any disclaimer, the term of this patent is extended or adjusted under 35 U.S.C. 154(b) by 1046 days.

(21) Appl. No.: 15/172,468

(22) Filed: Jun. 3, 2016

(65) Prior Publication Data

US 2016/0353795 A1    Dec. 8, 2016

Related U.S. Application Data

(60) Provisional application No. 62/170,726, filed on Jun. 4, 2015.

(51) Int. Cl.
*A24B 15/38* (2006.01)
*A24B 13/00* (2006.01)
(Continued)

(52) U.S. Cl.
CPC ............ *A24B 15/385* (2013.01); *A24B 13/00* (2013.01); *A24B 15/16* (2013.01); *A24B 15/167* (2016.11);
(Continued)

(58) Field of Classification Search
None
See application file for complete search history.

(56) References Cited

U.S. PATENT DOCUMENTS 5,869,505 A    9/1999    Keenan
2005/0176777 A1    8/2005    Williams et al.
(Continued)

FOREIGN PATENT DOCUMENTS

GB    892228    3/1962
JP    54151980 A    5/1978
(Continued)

OTHER PUBLICATIONS

Notification of Transmittal of the International Search Report and the Written Opinion of the International Searching Authority (Forms PCT/ISA/220, PCT/ISA/210 and PCT/ISA/237) issued on Aug. 30, 2016, by the European Patent Office in corresponding International Patent Application No. PCT/US2016/035637. (14 pages).
(Continued)

*Primary Examiner* — Phu H Nguyen
(74) *Attorney, Agent, or Firm* — Harness, Dickey & Pierce, P.L.C.

(57) ABSTRACT

A smokeless tobacco product or medicinal nicotine product including nicotine and acyl nornicotine. Preferably, the acyl nornicotine is selected from the group consisting of N-Pentanoylnornicotine, N-Hexanoylnornicotine, N-Heptanoylnornicotine, N-Octanoylnornicotine, N-Nonanoylnornicotine, N-Decanoylnornicotine, N-Undecanoylnornicotine, and N-Dedecanoylnornicotine. Also disclosed are methods of making such products.

18 Claims, 5 Drawing Sheets

N-Hexanoylnornicotine
$C_{15}H_{22}N_2O$
M.w. 246.348

N-Octanoylnornicotine
$C_{17}H_{26}N_2O$
M.w. 274.401

Nicotine
$C_{10}H_{14}N_2$
M.w. 162.23

(51) Int. Cl.
*A24B 15/16* (2020.01)
*A24B 15/167* (2020.01)
*A24B 15/28* (2006.01)
*A24F 23/02* (2006.01)
*A24F 40/10* (2020.01)
*A61K 9/00* (2006.01)
*A61K 9/50* (2006.01)
*A61K 31/465* (2006.01)
*A61M 11/04* (2006.01)
*H05B 3/00* (2006.01)

(52) U.S. Cl.
CPC ............ *A24B 15/282* (2013.01); *A24F 23/02* (2013.01); *A61K 9/007* (2013.01); *A61K 9/50* (2013.01); *A61K 31/465* (2013.01); *A61M 11/041* (2013.01); *H05B 3/0014* (2013.01); *A24F 40/10* (2020.01)

(56) References Cited

U.S. PATENT DOCUMENTS

| | | |
|---|---|---|
| 2007/0012328 A1 | 1/2007 | Winterson et al. |
| 2007/0261707 A1 | 11/2007 | Winterson et al. |
| 2008/0202533 A1 | 8/2008 | Mishra et al. |
| 2009/0038631 A1 | 2/2009 | Mishra et al. |
| 2009/0196834 A1* | 8/2009 | Andersen ............ A61K 9/0058 424/48 |
| 2009/0301505 A1 | 12/2009 | Liu et al. |
| 2010/0040679 A1 | 2/2010 | Chang et al. |
| 2010/0218779 A1* | 9/2010 | Zhuang ................ A24B 15/281 131/274 |
| 2010/0247586 A1 | 9/2010 | Hugerth et al. |
| 2011/0151035 A1 | 6/2011 | Wright, IV |
| 2012/0138074 A1* | 6/2012 | Cantrell ................ A24B 13/00 131/277 |
| 2012/0145170 A1 | 6/2012 | O'Connell |
| 2012/0305011 A1 | 12/2012 | Gonda |
| 2013/0298921 A1 | 11/2013 | Williams |
| 2014/0271946 A1 | 9/2014 | Kobal et al. |
| 2014/0345635 A1* | 11/2014 | Rabinowitz ............ A24F 40/50 131/352 |

FOREIGN PATENT DOCUMENTS

| | | |
|---|---|---|
| JP | 55019076 A * | 2/1980 |
| JP | 5759888 A | 9/1980 |
| JP | S571223 B2 | 1/1982 |
| JP | 5742634 B2 | 9/1982 |
| WO | 2014/125340 A1 | 8/2014 |

OTHER PUBLICATIONS

Database WPI, Week 198220, Thomson Scientific, London, GB; AN 1982-40417E, XP002760911 (Article Unavailable).

Matsuzaki et al., "Germination and Growth Inhibition of Acylnornicotines from Section Repandae of the Genius Nicotiana and Synthetic Acylnornicotines," Agric. Biol. Chem., 1988, pp. 1899-1903, vol. 52. No. 8.

Djordjevic et al., "Accumulation and Distribution of Acylated Nornicotine Derivatives in Flue-Cured Tobacco Alkaloid Isolines," J. Agric. Food Chem., 1990, pp. 347-350, vol. 38, American Chemical Society.

Burton et al., "Changes in Chemical Composition of Burley Tobacco during Sensescence and Curing. 2. Acylated Pyridine Alkaloids," J. Agric. Food Chem., 1988, pp. 579-584, vol. 36, American Chemical Society.

Andersen et al., "N'-Acyl and N'-Nitroso Pyridine Alkaloids in Alkaloid Lines of Burley Tobacco during Growth and Air-Curing," J. Agric. Food Chem., 1989, pp. 44-50, vol. 37, American Chemical Society.

* cited by examiner

N-Hexanoylnornicotine  
$C_{15}H_{22}N_2O$  
M.w. 246.348

N-Octanoylnornicotine  
$C_{17}H_{26}N_2O$  
M.w. 274.401

Nicotine  
$C_{10}H_{14}N_2$  
M.w. 162.23

ACYL NORNICOTINES REDUCE SENSORY IRRITATION IN TOBACCO AND NICOTINE PRODUCTS

SUMMARY

In an embodiment, tobacco product or medicinal nicotine product, comprising nicotine and acyl nornicotine.

In another embodiment, a method of making a tobacco product or medicinal nicotine product, comprising combining nicotine and acyl nornicotine.

In an additional embodiment the acyl nornicotine is present in a concentration ranging from about 0.04% to about 4.0% by weight of concentration.

DETAILED DESCRIPTION

As used herein, when it is said that a material does not exhibit a sensory effect, it means that an average adult consumer cannot detect a taste or irritation sensation (for example, burning, tingling, and/or cooling) arising from the material when using a portion of the product.

The term "edible" as used herein denotes the ability of a material or product to be enjoyed and at least partially consumed via the mouth. It includes products such as pouched tobacco wherein the product is not intended to be consumed in its entirety.

As used herein, the term "portion" denotes an amount of a product that would typically be used by an adult consumer as an individual serving and/or dose. For example, a portion refers to a single lozenge and/or a single puff from an inhaler.

The term "about" when used in conjunction with a stated numerical value or range denotes somewhat more or somewhat less than the stated value or range, to within a range of ±10% of that stated. In other embodiments, the term "about" indicates that the number differs from the given number by less than 9%, 8%, 7%, 6%, 5%, 4%, 3%, 2%, or 1%. Moreover, when reference is made to percentages in this specification, it is intended that those percentages are based on weight, i.e., weight percentages.

As used herein, the singular forms "a," "an," and "the" include plural reference unless the context clearly dictates otherwise.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

Acyl Nornicotine and Sensory Irritation

Nicotinic acetylcholine receptors are located on a variety of nerve endings in the peripheral nervous system and play a role in transmission of sensations of irritation, e.g., burning, to the brain. Nicotine, found in tobacco, can activate these receptors.

Activation of nerves by nicotine can lead to irritation sensations, varying with, e.g., the location, of these fibers in the gastrointestinal tract. For example, activation in the mouth can result in burning sensations, activation in the esophagus tends to result in a burning sensation and a bolus feel or in other instances hiccups and/or nausea, activation in the stomach would result in an urge to burp, etc.

Acyl nornicotines are generated in the tobacco leaf as an extension of the nicotine biosynthetic pathway. A percentage of nicotine is demethylated to form nornicotine which then can be N-acylated to form a variety of acyl nornicotines. Generally, acyl nornicotines are presented in the tobacco leaf at levels approximately 1% of the level of nicotine.

Example 1

Acyl-Nornicotine Reduced Sensory Irritation from Nicotine

The effect of pre-treatment with acyl nornicotine on sensory irritation from nicotine was tested using half-tongue test. N-Octanoylnornicotine was applied to tongues of human volunteers prior to application of a nicotine solution. Randomized sides of tongues were selected for application of liquid test sample or liquid control sample on filter paper. The liquid test sample or liquid control sample was applied to one side of a subject's tongue or the other. Blinded N-Octanoylnornicotine or water on filter paper was applied to the subject's tongue for 2 minutes, and then removed. Subjects noted a tingling or burning sensation on the side of the tongue where N-Octanoylnornicotine was applied. After a 30 second wait, filter papers with added nicotine solutions were applied to the spots on the tongue where the pretreatment filter papers had been applied. Over the following 2 minutes, subjects were asked to note sensory perceptions. Samples containing N-Octanoylnornicotine were at 10% of the level of the nicotine challenge samples. All perceived obvious reduction in irritation/burn on the side with the acyl nornicotine pre-treatment.

Preferably, the acyl nornicotine is present in a quantity so that it does not exhibit a sensory effect by itself (for example, excessive burning, detectable smell, and/or taste). Alternately, the product may be formulated so as to take advantage of inherent organoleptic properties of the acyl nornicotine, e.g., an acceptable level of perceived throat harshness.

Example 2

Figure 1:
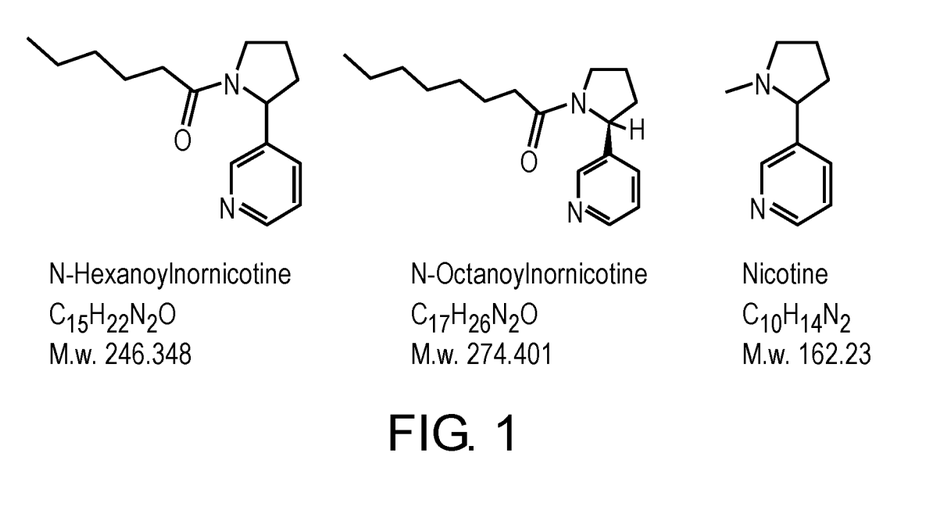
FIG. 1 shows the structure of nicotine, which is $C_{10}H_{14}N_2$ and has a molecular weight of 162.23 and of two specific acyl nornicotines: N-Hexanoylnornicotine, which is $C_{15}H_{22}N_2O$ and has a molecular weight of 246.348 and N-Octanoylnornicotine, which is $C_{17}H_{26}N_2O$ and has a molecular weight of 274.401.
Figure 2:
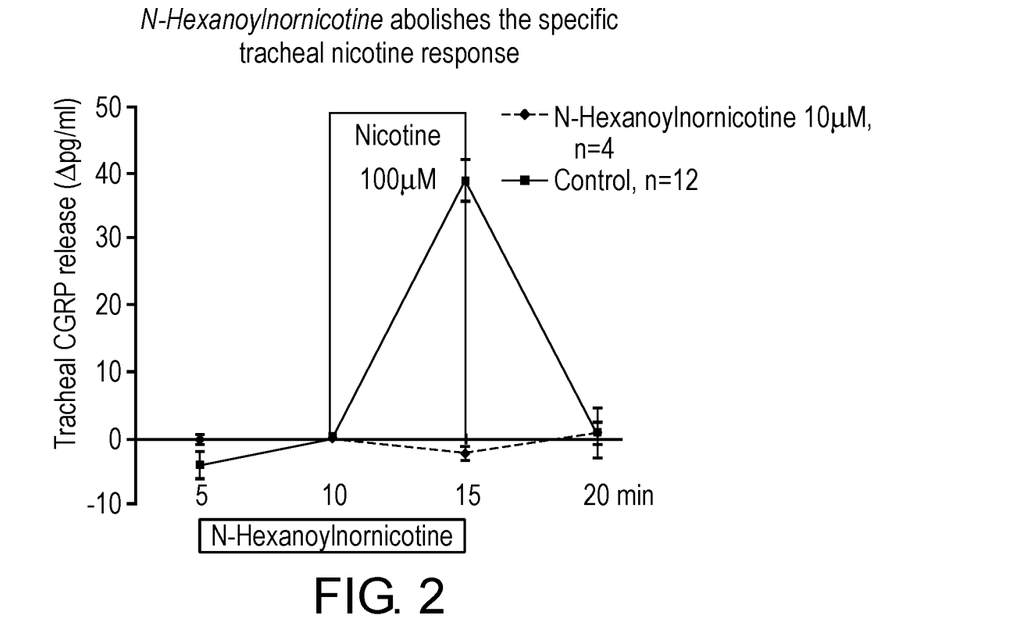
FIG. 2 shows results of N-Hexanoylnornicotine on the tracheal nicotine response. N-Hexanoylnornicotine abolishes the specific tracheal nicotine response. Mouse tracheal tissue samples are treated with N-Hexanoylnornicotine (10 μM) for 10 minutes. After five minutes of exposure, Nicotine (100 μM) is added to the tracheal tissue samples for the remaining five minutes of N-Hexanoylnornicotine exposure. CGRP release is measured for 15 minutes starting at the time point of N-Hexanoylnornicotine exposure. Control samples are exposed to Nicotine (100 μM) without the addition of N-Hexanoylnornicotine.
Figure 3:
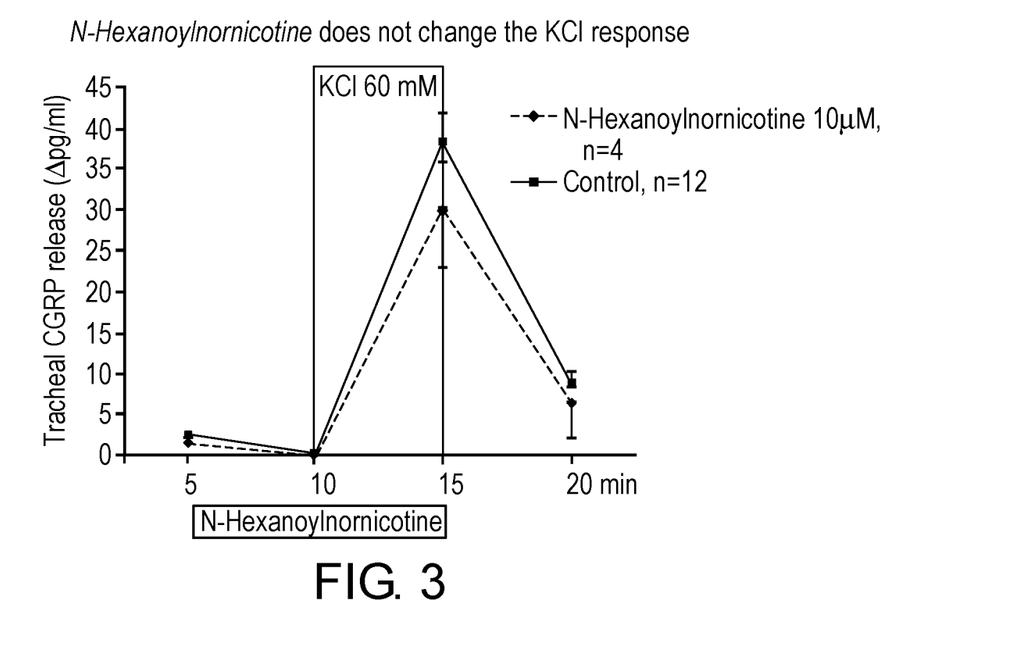
FIG. 3 shows results of N-Hexanoylnornicotine on the tracheal potassium chloride (KCl) response. N-Hexanoylnornicotine does not change the KCl response. As in FIG. 2, mouse tracheal tissue samples are treated with N-Hexanoylnornicotine (10 μM) for 10 minutes. After five minutes of exposure, KCl (60 mM) is added to the tracheal tissue samples for the remaining five minutes N-Hexanoylnornicotine exposure. CGRP release is measured for 15 minutes starting at the time point of N-Hexanoylnornicotine exposure. Control samples are exposed to KCl (60 mM) without the addition of N-Hexanoylnornicotine.
Figure 4:
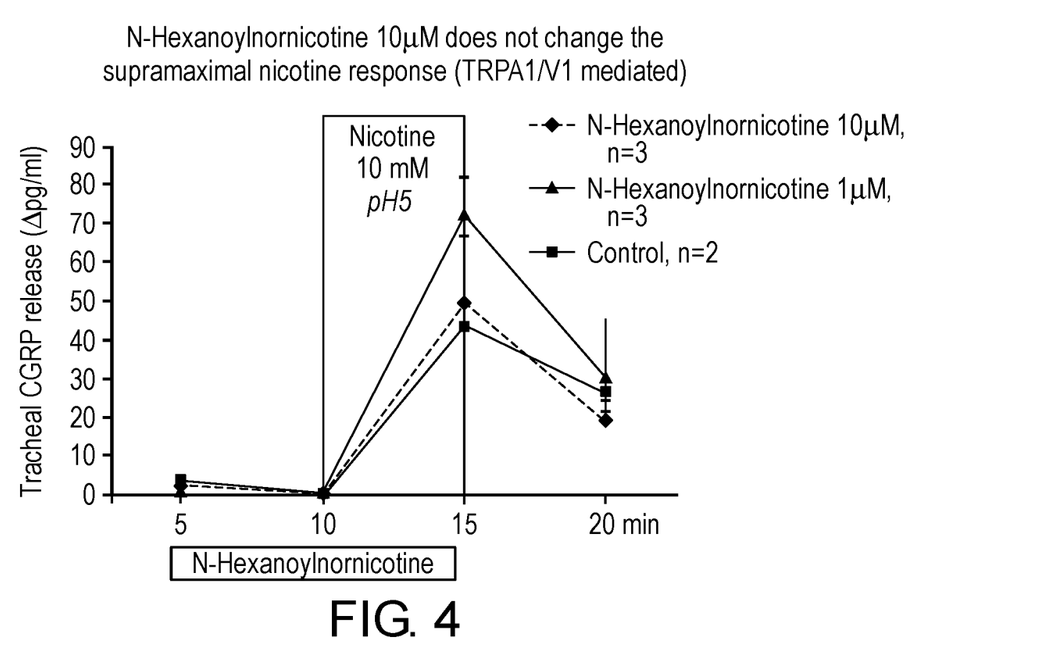
FIG. 4 shows results of N-Hexanoylnornicotine on the tracheal supramaximal nicotine response (Transient receptor potential cation channel member A1 or member V1 (TRPA1/V1) mediated). N-Hexanoylnornicotine (10 μM) does not change the tracheal supramaximal nicotine response. Mouse tracheal tissue samples are treated with 10 μM or 1 μM of N-Hexanoylnornicotine for 10 minutes. After five minutes of exposure, Nicotine (10 mM) is added to the tracheal tissue samples for five minutes. CGRP release is measured for 15 minutes starting at the time point of N-Hexanoylnornicotine exposure. Control samples are exposed to Nicotine (10 mM) without the addition of N-Hexanoylnornicotine.
Figure 5:
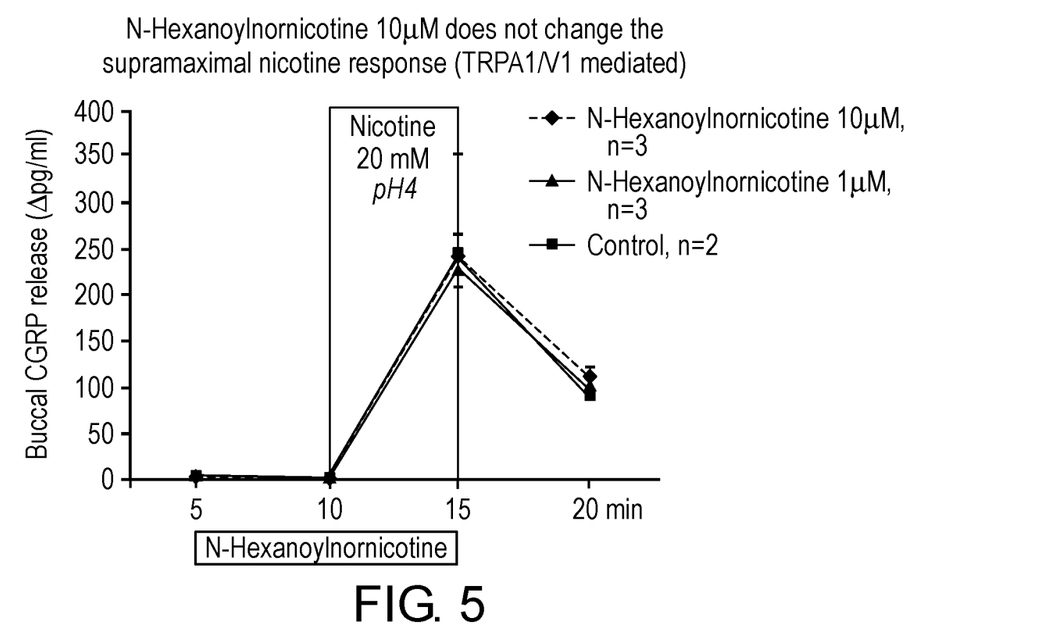
FIG. 5 shows results of N-Hexanoylnornicotine on the buccal supramaximal nicotine response (TRPA1/V1 mediated). N-Hexanoylnornicotine (10 μM) does not change the buccal supramaximal nicotine response. Mouse buccal tissue samples are treated with 10 μM or 1 μM of N-Hexanoylnornicotine for 10 minutes. After five minutes of exposure, Nicotine (10 mM) is added to the buccal tissue samples for five minutes. CGRP release is measured for 15 minutes starting at the time point of N-Hexanoylnornicotine exposure. Control samples are exposed to Nicotine (10 mM) without the addition of N-Hexanoylnornicotine.
Figure 6:
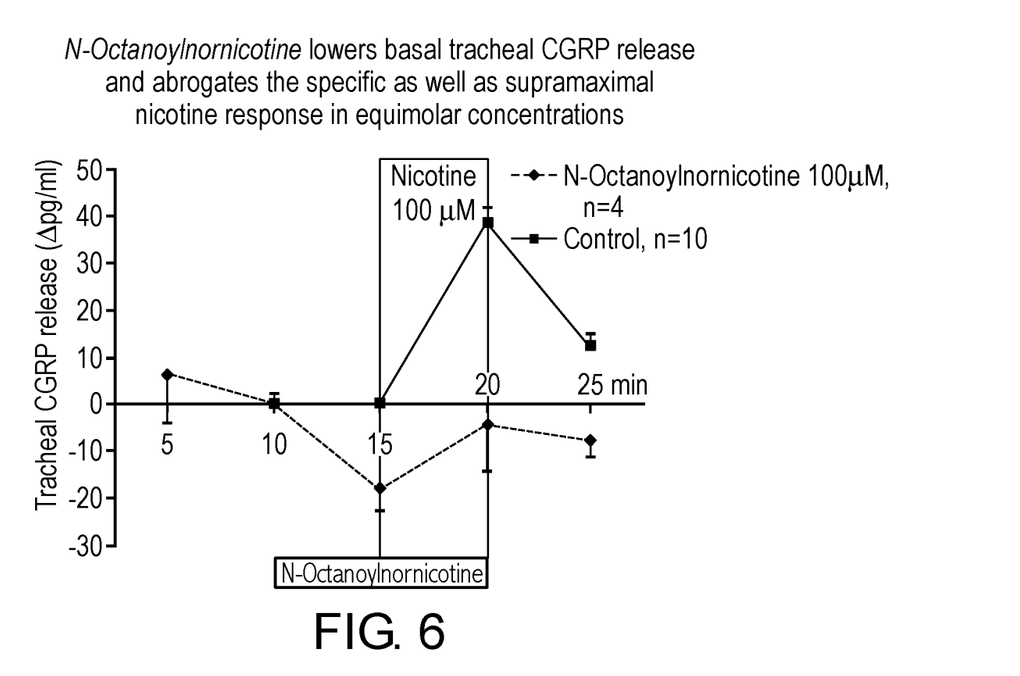
FIG. 6 shows results of N-Octanoylnornicotine on the tracheal nicotine response. N-Octanoylnornicotine lowers basal tracheal nicotine response and abrogates the specific tracheal nicotinic response in equimolar concentrations. Mouse tracheal tissue samples are treated with N-Octanoylnornicotine (100 μM) for 10 minutes. After 5 minutes of exposure to N-Octanoylnornicotine (100 μM), Nicotine (100 μM) is added to the tracheal tissue samples for five minutes. CGRP release is measured for 20 minutes starting five minutes prior to the time point of N-Octanoylnornicotine exposure. Control samples are exposed to Nicotine (100 μM) without the addition of N-Octanoylnornicotine.
Figure 7:
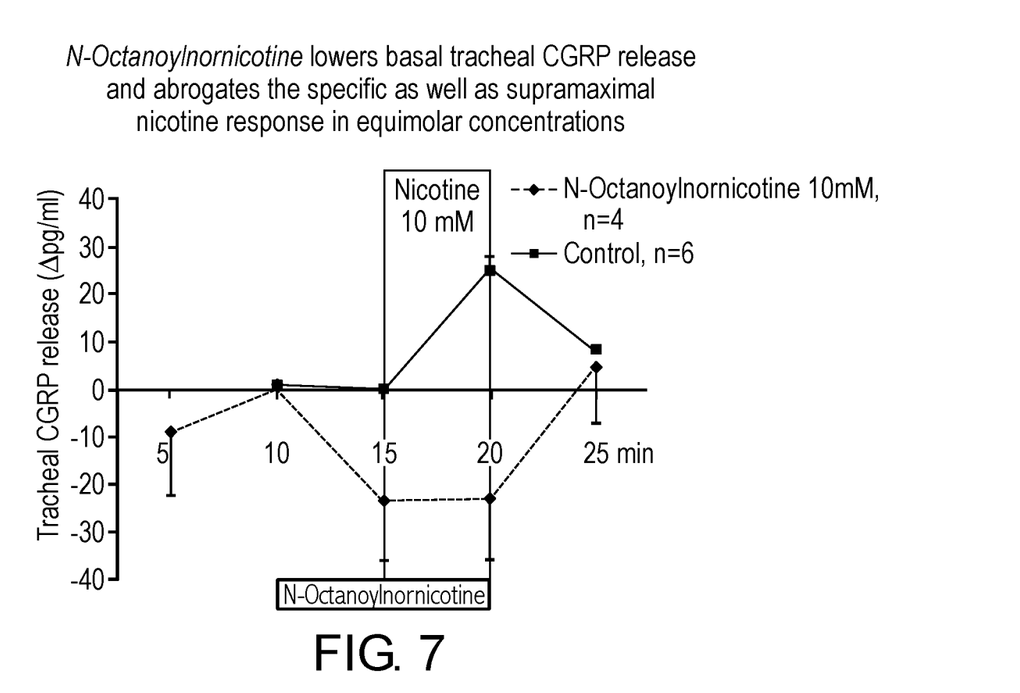
FIG. 7 shows results of N-Octanoylnornicotine on the tracheal nicotine response. N-Octanoylnornicotine abrogates the specific and supramaximal nicotine response in equimolar concentrations. Mouse tracheal tissue samples are treated with N-Octanoylnornicotine (10 mM) for 10 minutes. After 5 minutes of exposure of N-Octanoylnornicotine (10 mM), Nicotine (10 mM) is added to the tracheal tissue samples for five minutes. CGRP release is measured for 20 minutes starting five minutes prior to the time point of N-Octanoylnornicotine exposure. Control samples are exposed to Nicotine (10 mM) without the addition of N-Octanoylnornicotine.
Figure 8:
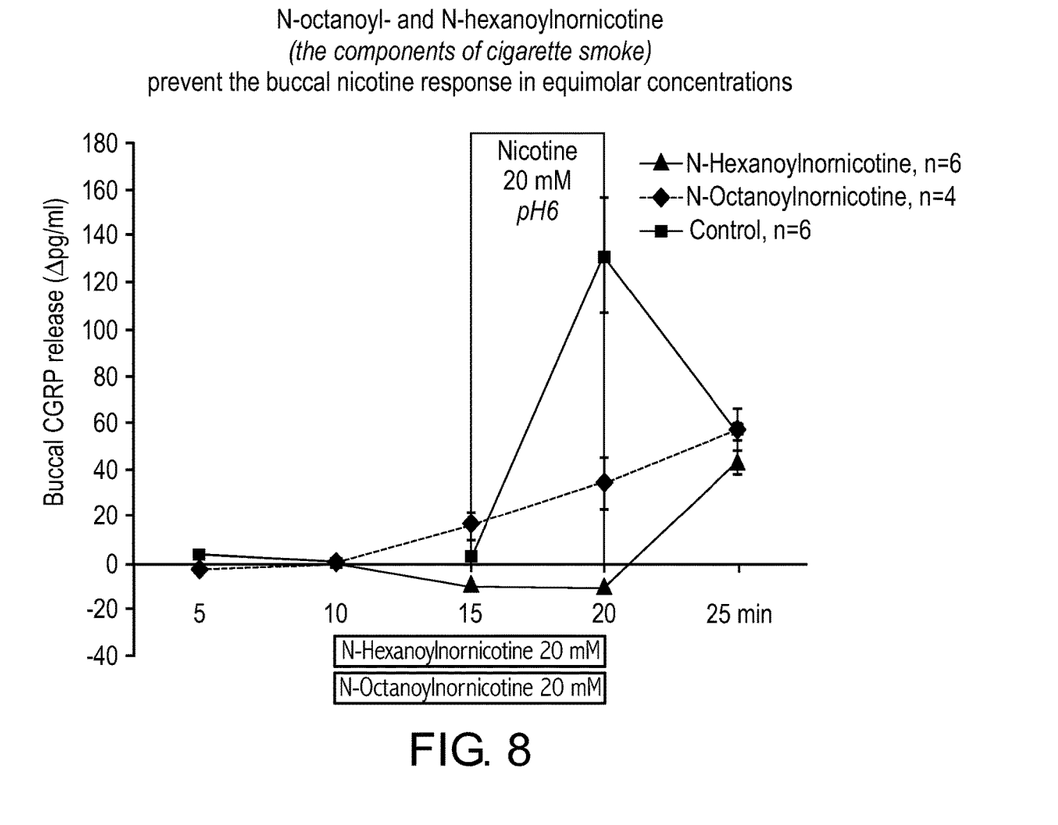
FIG. 8 shows results of N-Octanoylnornicotine and N-Hexanoylnornicotine on buccal nicotine response. N-Octanoylnornicotine and N-Hexanoylnornicotine prevent the buccal nicotine response in equimolar concentrations. Mouse buccal tissue samples were treated with N-Hexanoylnornicotine (20 mM) or N-Octanoylnornicotine (20 mM) for 10 minutes. After 5 minutes of exposure, Nicotine (20 mM) was added to the tracheal tissue samples for five minutes. CGRP release is measured for 20 minutes starting five minutes prior to the time point of N-Octanoylnornicotine and N-Hexanoylnornicotine exposure. Control samples are exposed to Nicotine (20 mM) without the addition of N-Octanoylnornicotine or N-Hexanoylnornicotine.

Acyl Nornicotine Reduces Nicotine Triggered Release of Calcitonin Gene-Related Peptide (CGRP) in Mouse Buccal and Tracheal Tissue FIGS. 2-8 show the results of studies on the effect of acyl nornicotine on nicotine triggered release of CGRP. CGRP is a biomarker of sensory irritation, specifically a marker of neurogenic inflammation. Tracheal or buccal mouse tissue samples were each treated with N-Hexanoylnornicotine or N-Octanoylnornicotine prior to exposure to nicotine or potassium chloride (KCl), used as a control. The test compounds were provided in a synthetic interstitial fluid and the release of CGRP was measured.

In both tracheal and buccal tissue preparations, a pretreatment of acyl nornicotine followed by application of nicotine plus acyl nornicotine, where the concentration of acyl nornicotine:nicotine was 1:1, showed complete inhibition of CGRP release. Studies further showed that a longer chain ($C_8$) acyl nornicotine was more potent than a shorter chain ($C_6$) acyl nornicotine. Additional experiments in buccal tissue showed that pretreatment of acyl nornicotine at 1:20,000 acyl nornicotine:nicotine produced some inhibition of CGRP release, ~50% inhibition at 1:2,000 acyl nornicotine:nicotine, and complete inhibition at 1:20 acyl nornicotine:nicotine.

Example 3

Acyl Nornicotines Inhibit Nicotine's Activation of the Nicotinic Acetylcholine Receptors α3β4

Human cell line HEK293 were designed to express human nicotinic acetylcholine receptor α3β4 (nACHR α3β4), which is a receptor associated with sensory irritation. These cells were plated on 96 well plates and acyl nornicotines were co-applied with a concentration of nicotine sufficient to yield 100% cell activation of the receptor. The influx of calcium into the cell is measured as an indicator of receptor activation. Similarly to the mouse tissue data shown above, longer chain ($C_8$) acyl nornicotine was more potent than shorter chain ($C_6$) acyl nornicotine; calcium influx was 50% inhibited at 1:100 acyl nornicotine:nicotine, and 100% inhibited at 1:10 acyl nornicotine:nicotine for the $C_8$ acyl nornicotine; calcium influx was 50% inhibited at 1:10 acyl nornicotine:nicotine, and 100% inhibited at 1:1 acyl nornicotine:nicotine for the $C_6$ acyl nornicotine. A summary of the results is presented in Table 1.

TABLE 1

| Cell Assay Results | | |
|---|---|---|
| Acyl Nornicotine | Inhibition (IC50 v 70 µM nicotine) | Activation (threshold) |
| Octanoyl Nornicotine | 0.5 µM | 1 mM |
| Hexanoyl Nornicotine | 5 µM | 10 mM |

Other Active Ingredients

Certain ingredients other than acyl nornicotines are also expected to perform as do acyl nornicotines, either by acting in the same manner as acyl nornicotines to inhibit nicotine-mediated activation, and/or by acting a precursor to a acyl nornicotine or another compound acting in the same manner as a acyl nornicotine. Such precursors are expected to be converted to active forms on human consumption, e.g., by metabolic enzymes.

In an embodiment, the role of acyl nornicotines as described herein is served by at least one compound selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, N-Dedecanoylnornicotine.

A Carrier System for Acyl Nornicotines

The inventors have found a carrier system for acyl nornicotines which can be advantageously used with a smokeless tobacco product or another product containing nicotine, such as a medicinal nicotine product and/or smoking cessation product. Such a system, when added to, e.g., a smokeless tobacco product, reduces or eliminates sensory irritation including burning, bolus feel in the esophagus, hiccups, and nausea.

The carrier system facilitates transport of acyl nornicotine to the sensory receptor sites where it exerts its effects, e.g., at TRPA1 and nicotinic acetylcholine receptors. Due to its chemical properties, acyl nornicotine reaches the receptors more reliably when the carrier system supports the transport of acyl nornicotine through several epithelial layers to reach the free nerve ending of afferent fibers of spinal or trigeminal (somatosensory) nerves or the vagal nerves.

As described above, acyl nornicotine was found successful in experimental settings in inhibiting such undesired sensations while dissolved in solutions, for example as applied to smokeless tobacco.

Without wishing to be bound by theory, it is believed that the reduction in irritation was due to acyl nornicotine-mediated reduction in activation of nicotinic acetylcholine receptors and/or of vanilloid receptors such as TRPV1 and/or TRPA1 receptors.

For medicinal nicotine preparations, such as smoking cessation products, it can be anticipated that patients' compliance will be substantially increased because of the reduction and elimination of unwanted side effects, thus potentially increasing the quitting success rates.

In an embodiment, a portion of a product includes a quantity of acyl nornicotine present in a concentration of about 0.04% to about 4.0% by weight concentration.

Smokeless Tobacco

As described herein, portions of smokeless tobacco include both pouched tobacco and pouchless portions that are free of a fabric and/or paper wrapper and comprise orally enjoyable tobacco that has been molded or divided into individual servings prior to use, such that the pre-portioned tobacco can be placed in an adult user's mouth without the need for the adult user to determine an amount to use. Pre-portioned, pouchless products of plant material, such as tobacco, are described in commonly-owned U.S. Patent Application Publication Nos. 2008/0202533, 2009/0038631, and 2009/0301505, each of which is incorporated by reference. Pouched portions are described in, e.g., U.S. Patent Application Publication Nos. 2007/0012328 and 2007/0261707, each of which is incorporated by reference.

Preferably, the portion has a generally rectangular or elliptical shape. Other preferred shapes for the pouch include any shape selected from the group consisting of polygons, squares, rectangles, circles, ovals, heart, star, half-moon, crescent, leaf shapes, and combinations thereof.

In a preferred embodiment, the portion is sized and configured to fit inside the mouth, between an adult user's cheek and gum. Preferably, the pouch takes a generally rectangular shape and is about 20 mm to about 35 mm long, about 10 mm to about 20 mm wide and about 3 mm to about 6 mm thick.

The acyl nornicotine may be applied to the exterior of a portion, either by itself or as part of a coating on the portion. Alternately, or in addition, the acyl nornicotine may be in an interior region of the portion.

Edible Tobacco Products

In another embodiment, the product is an edible tobacco product for tobacco enjoyment. An edible tobacco product can take the form of a tablet, lozenge, stick, chewable gum, spongy material, foam, cream, pellet, fiber, pill, capsule, pouched product, or combinations of these. Other examples of edible tobacco products include such chewable or non-chewable edible forms as tablets, gums, chocolates, flavored sponges, flavor strips, and the like.

Medicinal Nicotine Products

The product may be provided in a variety of forms. In an embodiment, the product is an edible product. An edible product, also referred to as "oral medicinal products", can take the form of a tablet, lozenge, stick, chewable gum, spongy material, foam, cream, pellet, fiber, pill, capsule, pouched products, or combinations of these. Other examples of edible products include such chewable or non-chewable edible forms as tablets, gums, chocolates, flavored sponges, flavor strips, and the like.

In another embodiment, a medicinal nicotine product or preparation is provided in a spray form, i.e., a sprayable product that allows an adult user to spray the acyl nornicotine into the mouth. If the product is to be administered in a spray form, the packaging preferably comprises an inhaler, such as a metered inhaler.

Tobacco Product or Medicinal Nicotine Product and Method of Making Such Products In one aspect, the present invention pertains to a tobacco product or medicinal nicotine product, comprising nicotine and a compound of Formula (I).

Formula (I) has the following structure, or its salt, in which R is $(C_5\text{-}C_{12})$-acyl, which is optionally substituted up to 3 times. In further embodiments, R is $C_5$-acyl, $C_6$-acyl, $C_7$-acyl, $C_8$-acyl, $C_9$-acyl, $C_{10}$-acyl, $C_{11}$-acyl, or $C_{12}$-acyl. In some embodiments, R is optionally substituted up to 3 times by either methyl, hydroxyl, amino, and/or a halogen. In other embodiments, R is an unsubstituted $C_6$-acyl or an unsubstituted $C_8$-acyl. In further embodiments, R is not $C_8$ substituted by hydroxyl at either C6 or C7.

In certain embodiments, the compound of Formula (I) is present in an amount effective to reduce or eliminate sensory irritation arising from consumption of the nicotine. In further embodiments, the compound of Formula (I) is in a concentration of about 0.04% to about 4.0% by weight of concentration. In other embodiments, the compound of Formula (I) is in a concentration of about 0.05% to about 3.75%, of about 0.1% to about 3.5%, of about 0.15% to about 3.25%, of about 0.2% to about 3.0%, of about 0.25% to about 2.75%, of about 0.3% to about 2.5%, of about 0.35% to about 2.25%, of about 0.4% to about 2.0%, of about 0.45% to about 1.75%, of about 0.5% to about 1.5%, or of about 0.55% to about 1.0% by weight of concentration. In other embodiments, the compound of Formula (I) is in a concentration of about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.41%, about 0.42%, about 0.43%, about 0.44%, about 0.45%, about 0.46%, about 0.47%, about 0.48%, about 0.49%, about 0.5%, about 0.51%, about 0.52%, about 0.53%, about 0.54%, about 0.55%, about 0.56%, about 0.57%, about 0.58%, about 0.59%, about 0.6%, about 0.61%, about 0.62%, about 0.63%, about 0.67%, about 0.68%, about 0.69%, about 0.7%, about 0.71%, about 0.72%, about 0.73%, about 0.74%, about 0.75%, about 0.76%, about 0.77%, about 0.78%, about 0.79%, about 0.8%, about 0.81%, about 0.82%, about 0.83%, about 0.84%, about 0.85%, about 0.86%, about 0.87%, about 0.88%, about 0.89%, about 0.9%, about 0.91%, about 0.92%, about 0.93%, about 0.94%, about 0.95%, about 0.96%, about 0.97%, about 0.98%, about 0.99%, about 1.0%, about 1.01%, about 1.02%, about 1.03%, about 1.04%%, about 1.05%, about 1.06%, about 1.07%, about 1.08%, about 1.09%, about 1.10%, about 1.11%, about 1.12%, about 1.13%, about 1.14%, about 1.15%, about 1.16%, about 1.17%, about 1.18%, about 1.19%, about 1.2%, about 1.21%, about 1.22%, about 1.23%, about 1.24%, about 1.25%, about 1.26%, about 1.27%, about 1.28%, about 1.29%, about 1.3%, about 1.31%, about 1.32%, about 1.33%, about 1.34%, about 1.35%, about 1.36%, about 1.37%, about 1.38%, about 1.39%, about 1.4%, about 1.41%, about 1.42%, about 1.43%, about 1.44%, about 1.45%, about 1.46%, about 1.47%, about 1.48%, about 1.49%, about 1.5%, about 1.51%, about 1.52%, about 1.53%, about 1.54%, about 1.55%, about 1.56%, about 1.57%, about 1.58%, about 1.59%, about 1.6%, about 1.61%, about 1.62%, about 1.63%, about 1.67%, about 1.68%, about 1.69%, about 1.7%, about 1.71%, about 1.72%, about 1.73%, about 1.74%, about 1.75%, about 1.76%, about 1.77%, about 1.78%, about 1.79%, about 1.8%, about 1.81%, about 1.82%, about 1.83%, about 1.84%, about 1.85%, about 1.86%, about 1.87%, about 1.88%, about 1.89%, about 1.9%, about 1.91%, about 1.92%, about 1.93%, about 1.94%, about 1.95%, about 1.96%, about 1.97%, about 1.98%, about 1.99%, about 2.0%, about 2.01%, about 2.02%, about 2.03%, about 2.04%%, about 2.05%, about 2.06%, about 2.07%, about 2.08%, about 2.09%, about 2.10%, about 2.11%, about 2.12%, about 2.13%, about 2.14%, about 2.15%, about 2.16%, about 2.17%, about 2.18%, about 2.19%, about 2.2%, about 2.21%, about 2.22%, about 2.23%, about 2.24%, about 2.25%, about 2.26%, about 2.27%, about 2.28%, about 2.29%, about 2.3%, about 2.31%, about 2.32%, about 2.33%, about 2.34%, about 2.35%, about 2.36%, about 2.37%, about 2.38%, about 2.39%, about 2.4%, about 2.41%, about 2.42%, about 2.43%, about 2.44%, about 2.45%, about 2.46%, about 2.47%, about 2.48%, about 2.49%, about 2.5%, about 2.51%, about 2.52%, about 2.53%, about 2.54%, about 2.55%, about 2.56%, about 2.57%, about 2.58%, about 2.59%, about 2.6%, about 2.61%, about 2.62%, about 2.63%, about 2.67%, about 2.68%, about 2.69%, about 2.7%, about 2.71%, about 2.72%, about 2.73%, about 2.74%, about 2.75%, about 2.76%, about 2.77%, about 2.78%, about 2.79%, about 2.8%, about 2.81%, about 2.82%, about 2.83%, about 2.84%, about 2.85%, about 2.86%, about 2.87%, about 2.88%, about 2.89%, about 2.9%, about 2.91%, about 2.92%, about 2.93%, about 2.94%, about 2.95%, about 2.96%, about 2.97%, about 2.98%, about 2.99%, 3.0%, about 3.01%, about 3.02%, about 3.03%, about 3.04%%, about 3.05%, about 3.06%, about 3.07%, about 3.08%, about 3.09%, about 3.10%, about 3.11%, about 3.12%, about 3.13%, about 3.14%, about 3.15%, about 3.16%, about 3.17%, about 3.18%, about 3.19%, about 3.2%, about 3.21%, about 3.22%, about 3.23%, about 3.24%, about 3.25%, about 3.26%, about 3.27%, about 3.28%, about 3.29%, about 3.3%, about 3.31%, about 3.32%, about 3.33%, about 3.34%, about 3.35%, about 3.36%, about 3.37%, about 3.38%, about 3.39%, about 3.4%, about 3.41%, about 3.42%, about 3.43%, about 3.44%, about 3.45%, about 3.46%, about 3.47%, about 3.48%, about 3.49%, about 3.5%, about 3.51%, about 3.52%, about 3.53%, about 3.54%, about 3.55%, about 3.56%, about 3.57%, about 3.58%, about 3.59%, about 3.6%, about 3.61%, about 3.62%, about 3.63%, about 3.67%, about 3.68%, about 3.69%, about 3.7%, about 3.71%, about 3.72%, about 3.73%, about 3.74%, about 3.75%, about 3.76%, about 3.77%, about 3.78%, about 3.79%, about 3.8%, about 3.81%, about 3.82%, about 3.83%, about 3.84%, about 3.85%, about 3.86%, about 3.87%, about 3.88%, about 3.89%, about 3.9%, about 3.91%, about 3.92%, about 3.93%, about 3.94%, about 3.95%, about 3.96%, about 3.97%, about 3.98%, about 3.99%, or about 4.0% by weight of concentration.

The compound of Formula (I) may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

In other embodiments, the present invention is directed to a tobacco product or medicinal nicotine product comprising nicotine and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, and N-Dedecanoylnornicotine.

In certain embodiments, the present invention is directed to a method of making a tobacco product or medicinal nicotine product, comprising combining nicotine and a compound of Formula (I).

In other embodiments, the present invention is directed to a method of making a tobacco product or medicinal nicotine product, comprising combining nicotine and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, and N-Dedecanoylnornicotine.

In further embodiments, the tobacco product is a smokeless tobacco product and the nicotine is disposed in a portion of smokeless tobacco; and wherein the tobacco product comprises either (1) a collection of tobacco particles at least partially enclosed by a coating comprising a water-soluble non-crosslinked component and a substantially water-insoluble cross-linked component, or (2) a pouch comprising smokeless tobacco enclosed in a water-permeable wrapper. In other embodiments, the tobacco product comprises the pouch and the compound of Formula (I) is in a coating on the wrapper of the pouch and/or applied to a component within the pouch wrapper. In still other embodiments, the tobacco product comprises a tobacco component at least partially enclosed by the coating, and the compound of Formula (I) is disposed in the coating.

In certain embodiments, the tobacco product is selected from the group consisting of chews, rods, bits, pouches, chewing tobacco, tablets, and capsules. In other embodiments, the medicinal nicotine product is selected from the group consisting of chewing gum and oral spray.

Liquid Aerosol Formulation and Electronic Smoking Article

In some embodiments, the present invention is directed to a liquid aerosol formulation for use in an electronic (vaping) smoking article comprising at least one aerosol former; water; and a compound of Formula (I). In further embodiments, the aerosol former is selected from the group consisting of propylene glycol, glycerin, and combinations thereof. In yet other embodiments, the aerosol former is included in an amount ranging from about 40% by weight based on the weight of the liquid formulation to about 90% by weight based on the weight of the liquid formulation, e.g., about 50% to about 80%, about 55% to about 75%, or about 60% to about 70%. In some embodiments, the liquid formulation can include propylene glycol and glycerin included in a ratio of about 3:2.

In yet further embodiments, the present invention is directed to an electronic smoking article operable to produce an aerosol of an enhanced organoleptic property, e.g., an acceptable level of perceived throat harshness at elevated levels of nicotine in a liquid formation (over about 2% by weight), the electronic smoking article comprising a supply of liquid formulation arranged to communicated with a heater, the heater operable to volatilize the liquid formulation, the liquid formulation comprising at least one aerosol former; water; and a compound of Formula (I). In other embodiments, R is optionally substituted up to 3 times by either methyl, hydroxyl, amino, and/or a halogen in the liquid aerosol formulation or the electronic smoking article. In yet other embodiments, R is an unsubstituted $C_6$ acyl or an unsubstituted $C_8$ acyl in the liquid aerosol formulation or the electronic smoking article. In further embodiments the R is not $C_8$ substituted by hydroxyl at either C6 or C7 in the liquid aerosol formulation or the electronic smoking article.

In still other embodiments, the elevated levels of nicotine in the liquid formulation is greater than about 2% by weight. In other embodiments, the elevated levels of nicotine in the formulation is greater than about 3%, about 4%, or about 5% by weight. In further embodiments, the elevated levels of nicotine in the formulation is less than about 3%, about 4%, about 5%, or about 6% by weight.

In other embodiments, the present invention is directed to a liquid aerosol formulation for use in an electronic smoking article comprising at least one aerosol former; water; and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, and N-Dedecanoylnornicotine.

In other embodiments, the present invention is directed to an electronic smoking (vaping) article operable to produce an aerosol of an enhanced organoleptic property (e.g., an acceptable level of perceived throat harshness at elevated levels of nicotine in the formulation (over 2% by weight)). The electronic smoking article preferably comprises a supply of liquid formulation arranged to communicated with a heater, the heater operable to volatilize the liquid aerosol formulation, the liquid aerosol formulation comprising at least one aerosol former; water; and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, and N-Dedecanoylnornicotine. In other embodiments, the present invention is directed to a method of improving an organoleptic property of an electronic smoking article comprising vaporizing a liquid aerosol formulation to form an aerosol, wherein the liquid aerosol formulation comprises at least one aerosol former; water; and a compound of Formula (I).

In certain embodiments, the present invention is directed to a method of replicating a sensory experience of a cigarette in an electronic smoking article comprising vaporizing a liquid aerosol formulation to form an aerosol, wherein the liquid aerosol formulation comprises at least one aerosol former; water; and a compound of Formula (I).

In other embodiments, the present invention is directed to a method of replicating a sensory experience of a cigarette in an electronic smoking article comprising vaporizing a liquid aerosol formulation to form an aerosol, wherein the liquid aerosol formulation comprises at least one aerosol former; water; and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, and N-Dedecanoylnornicotine.

In certain embodiments, the present invention is directed to a medicinal inhaler having an enhanced organoleptic property, comprising nicotine and a compound of Formula (I). In other embodiments, the present invention is directed to a medicinal inhaler having an enhanced organoleptic property (e.g., less perceived throat burn), comprising nicotine and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanolynornicotine, N-Octanoylnornicotine, N-Nonanoylnornicotine, N-Decanoylnornicotine, N-Undecanoylnornicotine, and N-Dedecanoylnornicotine.

In certain embodiments, the present invention is directed to a medicinal losenges, gums, and other orally administered medicinal nicotine delivery products ("oral medicinal products") having an enhanced organoleptic property, comprising nicotine and a compound of Formula (I). In other embodiments, the present invention is directed to an oral medicinal product having an enhanced organoleptic property, e.g., less perceived throat burn, comprising nicotine and an acyl nornicotine. In similar embodiments, the compound of Formula (I) is an acyl nornicotine. In further embodiments, the acyl nornicotine is selected from the group consisting of N-Pentanoylnornicotine, N-Hexanoylnornicotine, N-Heptanoylnornicotine, N-Octanoylnornicotine, N-Nonanoylnornicotine, N-Decanoylnornicotine, N-Undecanoylnornicotine, and N-Dedecanoylnornicotine.

While the foregoing has been described in detail with reference to specific embodiments thereof, it will be apparent to one skilled in the art that various changes and modifications may be made, and equivalents thereof employed, without departing from the scope of the claims.

What is claimed is:

1. A product, comprising:
nicotine, and
a compound of Formula (I), wherein the Formula (I) has the following structure, or a salt thereof, wherein R is ($C_5$-$C_{12}$)-acyl, which optionally has 1 to 3 substituents, the R is not $C_8$-acyl substituted by hydroxyl at either C6 or C7, and the product is a smokeless tobacco product with the nicotine disposed in a portion of the smokeless tobacco product the compound being present in the product in a concentration of 0.04% to 4.0% by weight.

2. The product of claim 1, wherein the R has 1 to 3 substituents, and the substituents are selected from the group consisting of methyl, hydroxyl, amino, and a halogen.

3. The product of claim 1, wherein the R is an unsubstituted $C_6$-acyl or an unsubstituted $C_8$-acyl.

4. The product of claim 1, wherein the smokeless tobacco product includes smokeless tobacco particles at least partially enclosed by a coating, the coating including a water-soluble non-crosslinked element and a substantially water-insoluble cross-linked element, and the compound is disposed in the coating.

5. The product of claim 1, wherein the smokeless tobacco product is selected from the group consisting of chews, rods, bits, pouches, chewing tobacco, tablets, and capsules.

6. The product of claim 1, wherein the R has 1 to 3 substituents, and the substituents are an amino, a halogen or both an amino and a halogen.

7. The product of claim 1, wherein a first carbon atom of the R is directly connected to the nitrogen atom of the pyrrolidine ring of Formula (I), and the first carbon atom is double-bonded to an oxygen atom.

8. The product of claim 1, wherein the smokeless tobacco product includes a pouch with smokeless tobacco particles enclosed in a wrapper, and the wrapper is water-permeable.

9. The product of claim 8, wherein the compound is in a coating, and the coating is on the wrapper of the pouch.

10. The product of claim 8, wherein the compound is in a coating, and the coating is applied to an element within the wrapper of the pouch.

11. The product of claim 8, wherein the smokeless tobacco particles are at least partially enclosed by a coating, and the compound is disposed in the coating.

12. The product of claim 1, wherein the R has 1 to 3 substituents, and the substituents are selected from the group consisting of hydroxyl, amino, and a halogen.

13. A product, comprising:
nicotine, and
a compound of Formula (I), wherein the Formula (I) has the following structure, or a salt thereof, wherein R is ($C_5$-$C_{12}$)-acyl, which has 1 to 3 substituents, the R is not $C_8$-acyl substituted by hydroxyl at either C6 or C7, and the product is a medicinal nicotine product that is selected from the group consisting of chewing gum and oral spray, the compound being present in the product in a concentration of 0.04% to 4.0% by weight.

14. The product of claim 13, wherein the substituents are an amino, a halogen or both an amino and a halogen.

15. An electronic article operable to produce an aerosol of an enhanced organoleptic property, the electronic article comprising:
a supply of a formulation arranged to communicate with a heater, the heater operable to volatilize the formulation, the formulation comprising:
at least one aerosol former;
water; and
a compound of Formula (I), wherein the Formula (I) has the following structure, or a salt thereof, wherein R is ($C_5$-$C_{12}$)-acyl, which has 1 to 3 substituents, the R is not $C_8$-acyl substituted by hydroxyl at either C6 or C7, and the substituents are selected from the group consisting of methyl, hydroxyl, amino, and a halogen, the compound being present in the formulation in a concentration of 0.04% to 4.0% by weight.

16. The electronic article of claim 15, wherein the substituents are an amino, a halogen, or both an amino and a halogen.

17. The electronic article of claim 15, wherein a first carbon atom of the R is directly connected to the nitrogen atom of the pyrrolidine ring of Formula (I), and the first carbon atom is double-bonded to an oxygen atom.

18. An electronic article operable to produce an aerosol of an enhanced organoleptic property, the electronic article comprising:
a supply of a pre-vapor formulation arranged to communicate with a heater, the heater operable to volatilize the pre-vapor formulation, the pre-vapor formulation comprising:
at least one aerosol former;
water; and
a compound of Formula (I), wherein the Formula (I) has the following structure, or a salt thereof, wherein R is an unsubstituted $C_6$-acyl or an unsubstituted $C_8$-acyl, and the compound is present in the pre-vapor formulation in a concentration of about-0.04% to about-4.0% by weight of concentration.

* * * * *